United States Patent
Lin et al.

(10) Patent No.: US 9,463,442 B2
(45) Date of Patent: Oct. 11, 2016

(54) CATALYST, METHOD OF MANUFACTURE AND USE THEREOF

(75) Inventors: Zhonjie Lin, Manchester (GB); Jonathan Keith Bartley, South Glamorgan (GB); Stuart Hamilton Taylor, South Glamorgan (GB); Graham John Hutchings, Ross on Wye (GB); Nicholas Francois Dummer, South Glamorgan (GB)

(73) Assignee: UNIVERSITY COLLEGE CARDIFF CONSULTANTS LIMITED, South Glamorgan (GB)

( * ) Notice: Subject to any disclaimer, the term of this patent is extended or adjusted under 35 U.S.C. 154(b) by 384 days.

(21) Appl. No.: 13/818,456

(22) PCT Filed: Aug. 12, 2011

(86) PCT No.: PCT/GB2011/051528
§ 371 (c)(1),
(2), (4) Date: Oct. 4, 2013

(87) PCT Pub. No.: WO2012/025737
PCT Pub. Date: Mar. 1, 2012

(65) Prior Publication Data
US 2014/0024525 A1    Jan. 23, 2014

(30) Foreign Application Priority Data
Aug. 25, 2010   (GB) .................................. 1014185.1

(51) Int. Cl.
B01J 23/32   (2006.01)
B01J 23/16   (2006.01)
B01J 23/881  (2006.01)
(Continued)

(52) U.S. Cl.
CPC ............... *B01J 23/881* (2013.01); *B01J 23/28* (2013.01); *B01J 23/30* (2013.01); *B01J 23/34* (2013.01); *B01J 23/686* (2013.01); *B01J 23/882* (2013.01); *B01J 23/888* (2013.01); *B01J 35/006* (2013.01); *B01J 35/008* (2013.01); *B01J 35/023* (2013.01); *B01J 35/026* (2013.01); *B01J 35/06* (2013.01); *B01J 35/1009* (2013.01); *B01J 35/1014* (2013.01); *B01J 37/02* (2013.01);
(Continued)

(58) Field of Classification Search
CPC ........ B01J 23/881; B01J 23/28; C07C 45/38
USPC ........................................ 502/316, 321, 305
See application file for complete search history.

(56) References Cited

FOREIGN PATENT DOCUMENTS

| CN | 101 423 260 A | 5/2009 |
|---|---|---|
| EP | 1674156 A1 | 12/2005 |

OTHER PUBLICATIONS

Paraguay-Delgado, F. et al. "Optimization of the Synthesis of a-MoO3 Nanoribbons and Hydrodesulfurization (HDS)" Catalyst Test; Journal of Nanoscience and Nanotechnology, vol. 7, 3677-3683, 2007.

(Continued)

*Primary Examiner* — Matthew E Hoban
*Assistant Examiner* — James Fiorito
(74) *Attorney, Agent, or Firm* — Charles C. Achkar; Ostrolenk Faber LLP

(57) ABSTRACT

A catalyst is provided, the catalyst comprising rods having mean length of 100 microns or less, the rods comprising a metal molybdate or tungstate, the metal being selected from the group consisting of iron, manganese, nickel, chromium, vanadium, aluminum, silver, titanium, copper, bismuth, and cobalt. A method of making such a catalyst is also provided.

19 Claims, 5 Drawing Sheets

(51) Int. Cl.
| | |
|---|---|
| B01J 23/882 | (2006.01) |
| B01J 23/888 | (2006.01) |
| B01J 35/00 | (2006.01) |
| B01J 35/02 | (2006.01) |
| B01J 35/06 | (2006.01) |
| B01J 35/10 | (2006.01) |
| B01J 37/02 | (2006.01) |
| C07C 45/27 | (2006.01) |
| B01J 23/28 | (2006.01) |
| B01J 23/30 | (2006.01) |
| B01J 23/34 | (2006.01) |
| B01J 23/68 | (2006.01) |
| C07C 45/38 | (2006.01) |

(52) U.S. Cl.
CPC .......... *B01J 37/0207* (2013.01); *C07C 45/27* (2013.01); *C07C 45/38* (2013.01); *B01J 2523/69* (2013.01)

(56) References Cited

OTHER PUBLICATIONS

Lei, Shuijin et al., "Preparation of manganese molybdate rods and hollow olive-like spheres"; J. Mater Sci. (2006) 41:4737-4743.

Bowker, Michael et al., "The Selective Oxidation of Methanol on Iron Molybdate Catalysts", Top Catal. (2008) 48:158-165; Published online: Mar. 27, 2008 © Springer Science+Business Media, LLC 2008 48:158-165.

Phuruangrata, Anukorn et al., "Electrochemical hydrogen evolution over Mo03 nanowires produced by microwave-assisted hydrothermal reaction", Electrochemistry Communications 11 (2009) pp. 1740-1743.

Ding Yi, et al., "General Synthesis and Phase Control of Metal Moiybdate Hydrates MMoO4 • $n$H20 (M=Co, Ni, Mn, n=0, 3/4, 1) Nano/Microcrystals by a Hydrothermal Approach: Magnetic, Photocatalytic, and Electrochemical Properties", Inorganic Chemistry, vol. 47, No. 17, 2008, pp. 7813-7823.

C. V. Subba Reddy, et al., "Characterization of MoO3 nanobelt cathode for Li-battery applications", Appl. Phys. A 89, pp. 995-999 (2007).

C. V. Subba Reddy et al., "Characterization of MoO3 nanorods for lithium battery using PVP as a surfactant", J. Solid. State Electrochem. (2009) 13:1945-1949.

Raidongia, Kalyan et al. "Synthesis and characterization of metal oxide nanorod brushes," Bull. Mater. Sci., vol. 31, No. 1, Feb. 2008, pp. 87-92.

Li, Wang et al., "Preparation, Characterization, and Properties of Ferric Molybdate Nanotubes for Propene Epoxidation by Air", Chin. J. Catal., 2009, 30(8): 711-713.

Li Wang et al., "Ferric molybdate nanotubes synthesized based on the Kirkendall effect and their catalytic property for propene epoxidation by air," Chem. Commun., 2009, pp. 1565-1567.

Xiong Wen Lou et al., "Complex β-MoO3 Nanostructures with External Bonding Capacity for Self-Assembly", J., Am. Chem. Soc., 2003, vol. 125, pp. 2697-2704.

Xiong Wen Lou et al., "Hydrothermal Synthesis of β-MoO3 Nanorods via Acidification of Ammonium Heptamolybdate Tetrahydrate", Chem. Mater., vol. 14, No. 11. 2002, pp. 4781-4789.

Liqiang Mai et al., "Lithiated MoO3 Nanobelts with Greatly Improved Performance for Lithium Batteries," Advanced Materials, 2007, vol. 19, pp. 3712-3716.

Adkins, Homer et al., "The Oxidation of Methanol With Air Over Iron, Molybdenum, and Iron—Molybdenum Oxides", Apr. 1931, vol. 53, pp. 1512-1520.

Ji Chan Park et al., "Synthesis of Polyerystalline Mo/MoO$x$ Nanoflakes and Their Transformation to MoO3 and MoS2 Nanoparticles," Chem. Mater., 2007, vol. 19, No. 11, pp. 2706-2708.

Michailovski, A. et al., "Hydrothermal Synthesis of Molybdenum Oxide Based Materials: Strategy and Structural Chemistry", Chem. Eur. J. 2006,vol. 12, pp. 9122-9134.

International Search Report for PCT/GB2011/051528 (Jan. 16, 2012).

Search Report under Section 17 for GB1014185.1, 2010.

CATALYST, METHOD OF MANUFACTURE AND USE THEREOF

This application is the United States national phase filing of the corresponding international application number PCT/GB2011/051528, filed on Aug. 12, 2011, which claims priority to and benefit of GB Application No. 1014185.1, filed Aug. 25, 2010, which applications are hereby incorporated by reference in their entirety.

The present invention relates to a catalyst, particularly (but not exclusively) catalysts comprising iron molybdate.

It is known to use iron molybdate to catalyse selective oxidation reactions. The conventional catalyst (such as that supplied by Perstop® AB, BASF® and Sud-Chemie®) is in a particulate form and has a relatively low surface area. Iron molybdate catalysts with a higher surface area have been made, such as the tubular structures described by Wang et al. in "Ferric molybdate nanotubes synthesized based on the Kirkendall effect and their catalytic property for propene oxidation by air", Chem. Commun., 2009, 1565-1567. It is believed that such tubular structures may be fragile and therefore difficult to store and handle. The present invention seeks to mitigate one or more of the problems mentioned above.

In accordance with a first aspect of the present invention, there is provided a catalyst comprising rods having a mean length of 100 microns or less, the rods comprising a metal molybdate or tungstate.

The catalyst of the first aspect of the present invention has been found to be unexpectedly effective, and for certain reactions, can be as effective as commercially available catalysts, which is surprising given that it is expected that the catalyst of the first aspect of the present invention may be optimised further.

It is preferred that said metal of the metal molybdate or tungstate is selected from the group consisting of iron, manganese, nickel, chromium, vanadium, aluminium, silver, titanium, copper, bismuth and cobalt.

The term "rod" is to be taken to have its usual geometric meaning i.e. that of an elongate, solid shape, without avoid extending through the shape, in contrast to a tube which has an elongate shape but has a void extending through the length of the shape. A "rod" is typically generally cylindrical i.e. has approximately the same cross-sectional shape and size along the length of the shape. The rod may be any suitable cross-sectional shape, such as square, hexagonal or circular.

It is preferred that the rods comprise a metal molybdate.

It is preferred that the metal is selected from the group consisting of iron, manganese, bismuth and cobalt.

The rods may have a mean length of 50 microns or less, optionally 25 microns or less, further optionally 15 microns or less and further more optionally a mean length of from 3 to 15 microns.

The rods may have a mean greatest dimension in a direction normal to the length of the rod of at least 0.1 microns, optionally at least 0.2 microns, further optionally from 0.2 microns to 5 microns and further more optionally from 0.2 microns to 2 microns.

The ratio of the mean length of the rods to the mean greatest dimension in a direction normal to the length of the rod may be from 3:1 to 1000:1, optionally from 3:1 to 100:1, further optionally from 5:1 to 50:1 and further more optionally from 5:1 to 30:1.

The rods may have an aspect ratio of from 4 to 500, optionally from 3 to 100, further optionally from 5 to 50 and further more optionally from 5 to 30.

The rods may comprise a further metal catalyst. For example, the rod may comprise iron molybdate or tungstate and a further metal catalyst, such as cobalt. The cobalt may be provided as cobalt molybdate or tungstate. The further metal catalyst may be provided as metal oxide.

The catalyst may have a mean surface area of at least 2 $m^2g^{-1}$, optionally at least 5 $m^2g^{-1}$ and further optionally at least 10 $m^2g^{-1}$. The mean surface area may typically be measured using the standard BET method with adsorption of nitrogen gas.

If the metal molybdate or tungstate is iron molybdate or tungstate, the molar ratio of iron to molybdenum in the rods may be from 0.01:1 to 0.5:1, optionally from 0.01:1 to 0.3:1 and further optionally from 0.03:1 to 0.2:1. Such a molar ratio is obtained by considering the total volume of a rod, not just part of the volume of a rod.

If the metal molybdate or tungstate is iron molybdate or tungstate, the molar ratio of iron to molybdenum at the surface of the rods may be from 0.1:1 to 0.67:1, optionally from 0.2:1 to 0.5:1 and further optionally from 0.3:1 to 0.5:1. The ratio may be conveniently measured using x-ray photoelectron spectroscopy (XPS).

The molar ratio of said metal to molybdenum or tungsten on the surface of the rods may be greater than in the centre of the rods. The concentration of said metal may be greater at the surface of the rods than in the centre of the rods.

The centre of the rods may be substantially devoid of said metal (and preferably devoid of the metal molybdate or tungstate).

The rods may comprise a central region which is substantially devoid of said metal (and preferably devoid of the metal molybdate or tungstate) and an outer region comprising said metal (preferably in the form of the metal molybdate or tungstate). The volume of the outer region may be less than about 500% of the volume of the central region, optionally less than about 300%, optionally less than about 100%, optionally less than about 50%, optionally less than about 30% and further optionally less than about 10% of the volume of the central region.

The concentration of said metal (preferably in the form of the molybdate or tungstate) may be higher in the outermost part of the outer region than in the innermost part of the outer region.

At least 95% of said metal content of the rods (and preferably 95% of the metal molybdate or tungstate content) may be found in the outer 80% of the volume of the rods, optionally in the outer 60%, optionally in the outer 40%, optionally in the outer 20% and further optionally in the outer 10% of the volume of the rods.

The rods may comprise "islands" of metal molybdate or tungstate. For example, if the rods comprise outer regions comprising metal molybdate, the outer regions may comprise regions or islands of metal molybdate and regions which do not comprise metal molybdate.

The rods may comprise islands of metal molybdate or tungstate which project from the rod. The islands may typically have a mean greatest dimension of from 10 to 100 nm, and optionally have a mean greatest dimension of from 30 to 70 nm. The islands are typically in the form of projections or bulges. The islands are typically discrete i.e. separate from one another.

The mean density of said islands may typically be from 20 to 100 islands per rod.

The catalyst may optionally be substantially free of iron oxide.

In accordance with a second aspect of the present invention, there is provided a method of making a catalyst comprising:
(i) Providing rods comprising molybdenum or tungsten oxide;
(ii) Depositing metal on the rods comprising molybdenum or tungsten oxide, and
(iii) Heating the product of step (ii) to produce rods comprising metal molybdate or tungstate.

The method of the second aspect of the present invention may be used to make the catalyst of the first aspect of the present invention.

Said metal may be selected from the group consisting of iron, manganese, nickel, chromium, copper, bismuth, vanadium, aluminium, silver, titanium and cobalt.

The rods provided in step (i) may comprise molybdenum (VI) oxide, for example. The rods in step (i) may comprise tungsten (VI) oxide. It is preferred that the rods provided in step (i) comprise at least 70% (optionally at least 80%, further optionally at least 90%) by weight of molybdenum or tungsten oxide.

If the rods provided in step (i) comprise molybdenum oxide, the rods provided in step (i) may be commercially available or may produced by admixing particulate molybdenum oxide with hydrogen peroxide. The particulate molybdenum oxide typically has a non rod-like morphology which is typically displayed by commercially-available off-the-shelf molybdenum oxide. The mixture of particulate molybdenum oxide and hydrogen peroxide may be heated, optionally at greater than ambient pressure. The admixture may be heated in an autoclave, for, example.

Those skilled in the art will realise that the metal deposited in step (ii) is typically not elemental metal i.e. metal having a zero oxidation state.

If the rods provided in step (i) comprise molybdenum oxide, the rods provided in step (i) may be produced by admixing particulate $(NH_4)_6Mo_7O_{24}$ with nitric acid. The particulate $(NH_4)_6Mo_7O_{24}$ typically has a non rod-like morphology which is typically displayed by commercially-available off-the-shelf $(NH_4)_6Mo_7O_{24}$. The mixture of particulate $(NH_4)_6Mo_7O_{24}$ and nitric acid may be heated, optionally at greater than ambient pressure. The admixture may be heated in an autoclave, for example.

The rods provided in step (i) may have a mean length of 50 microns or less, optionally 25 microns of less, further optionally 15 microns or less and further more optionally a mean length of from 3 to 15 microns.

The rods provided in step (i) may have a mean greatest dimension in a direction normal to the length of the rod of at least 0.1 microns, optionally at least 0.2 microns, further optionally from 0.2 microns to 5 microns and further more optionally from 0.2 microns to 2 microns.

The ratio of the mean length of the rods provided in step (i) to the mean greatest dimension in a direction normal to the length of the rod may be from 3:1 to 1000:1, optionally from 3:1 to 100:1, further optionally from 5:1 to 50:1 and further more optionally from 5:1 to 30:1.

The rods provided in step (i) may have an aspect ratio of from 4 to 500, optionally from 3 to 100, further optionally from 5 to 50 and further more optionally from 5 to 30.

The metal deposited in step (ii) is typically deposited by admixing the rods comprising molybdenum or tungsten oxide with a solution of ions of the metal. The counterions to the metal ions may comprise one or more of chloride, bromide, fluoride, iodide and nitrate, preferably nitrate. The product of step (ii) may be removed from solution prior to heating in step (iii). The amount of solution provided may merely be sufficient to wet the rods comprising molybdenum or tungsten oxide. In this case, there should be no excess solution, sufficient solution being added to make the rods tacky. This technique is known to those skilled in the art as incipient wetness impregnation. Therefore, step (ii) may comprise subjecting the rods comprising molybdenum or tungsten oxide to incipient wetness impregnation with a solution of ions of the metal.

The relative molar ratios of molybdenum or tungsten to the metal content of the solution may optionally be from 1.8:1 to 15:1, optionally from 1.8:1 to 8:1, further optionally from 1.8:1 to 6:1, more optionally from 2:1 to 4:1 and further more optionally about 2.2:1. Such ratios are typically calculated based on the relative amount of reagents.

The method may comprise adding a further metal. For example, the catalyst so made may comprise an iron molybdate or tungstate and a further metal, such as cobalt. The cobalt may form in the catalyst as cobalt molybdate or tungstate.

The further metal may be added in step (ii) or subsequent to step (ii) but before step (iii).

Step (iii) may comprise heating in a gaseous atmosphere, optionally in air. Step (iii) may act to calcine the product of step (ii). Step (iii) may comprise heating at a temperature of from 300° C. to 700° C., optionally from 350° C. to 600° C., optionally from 400° C. to 550° C., optionally from 425° C. to 530° C., further optionally from 425° C. to 510° C. and more optionally from 440° C. to 505° C. Step (iii) may comprise heating for a period of from 30 minutes to 5 hours, optionally from 1 hour to 4 hours and further optionally from 1 hour to 3 hours.

In accordance with a third aspect of the present invention, there is provided a catalyst makeable using a method in accordance with the second aspect of the present invention.

In accordance with a fourth aspect of the present invention, there is provided the use of rods comprising metal molybdate or tungstate as a catalyst, the rods having a mean length of 100 microns or less.

Said metal may be selected from the group consisting of iron, manganese, copper, bismuth, nickel, chromium, vanadium, aluminium, silver, titanium and cobalt.

The following reactions may be catalysed:
Selective oxidation (in particular, the selective oxidation of alcohols to aldehydes, such as methanol to methanal), hydrodesulphurisation and hydrodenitrogenation.

The rods used may comprise those features described above in relation to the method of the first aspect of the present invention.

The invention will now be described by way of example only with reference to the following figures of which:

Figure 3:
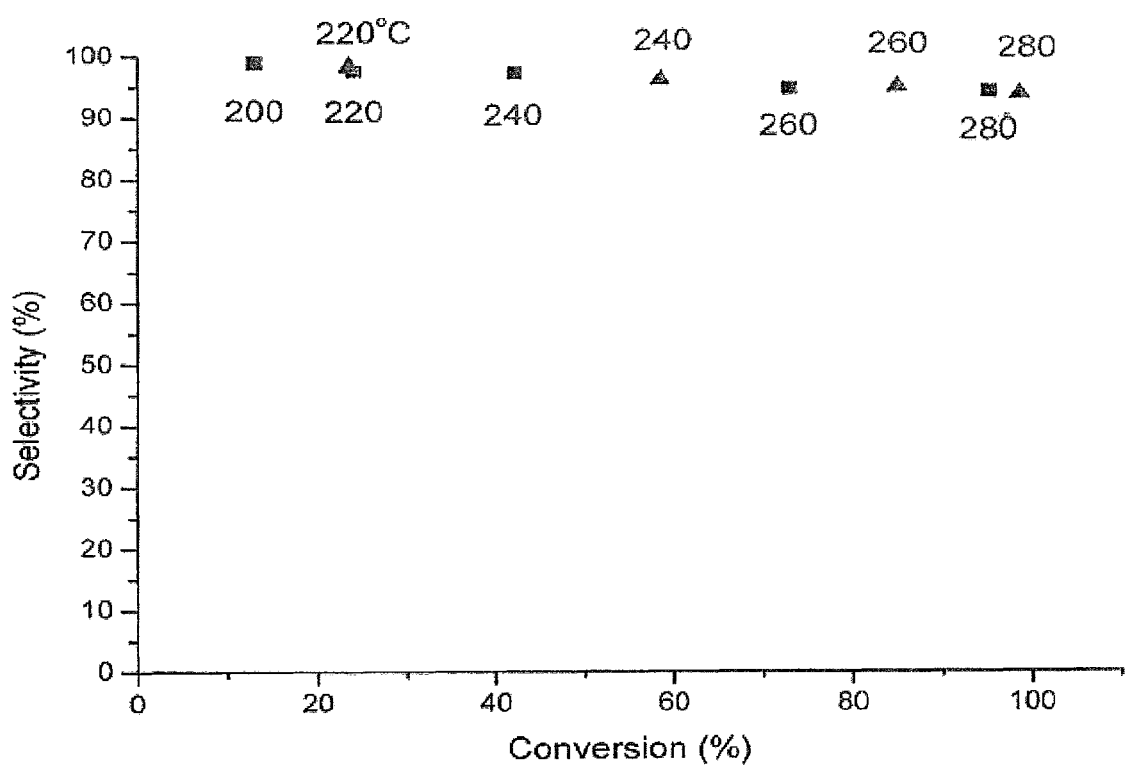
Figure 4:
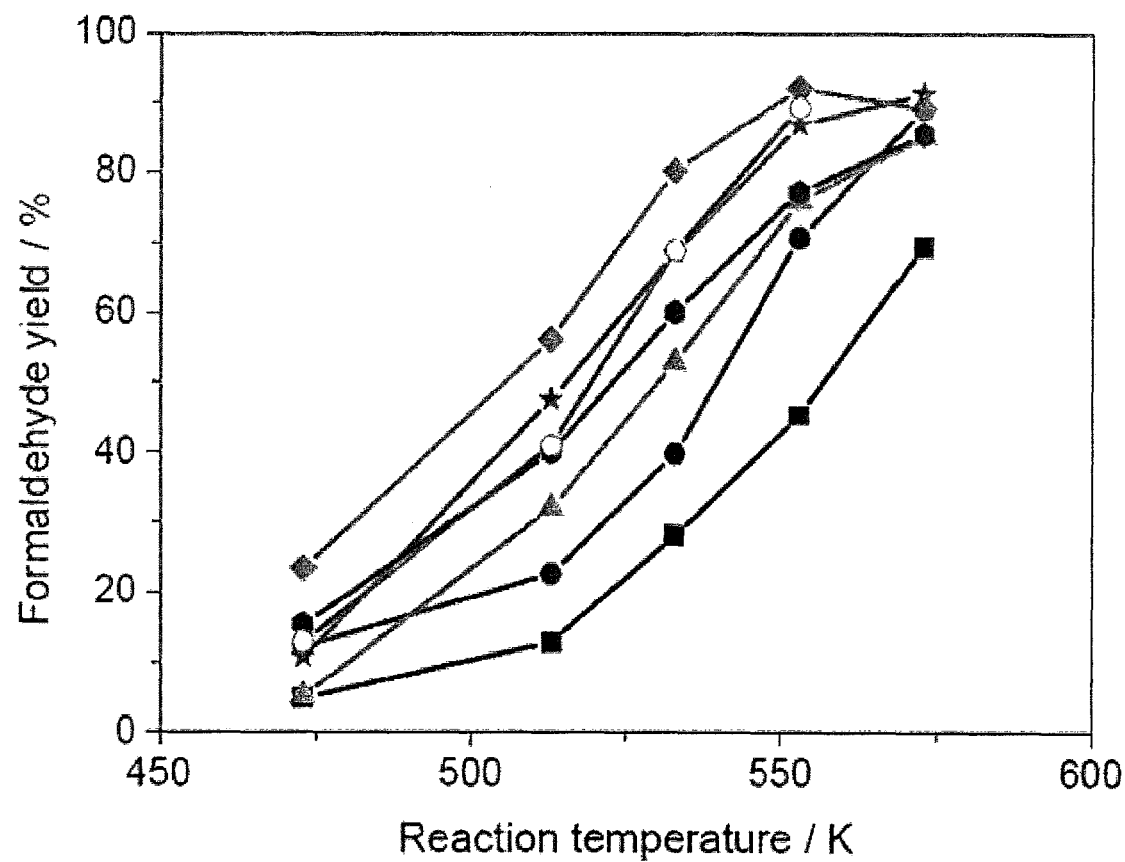
Figure 5:
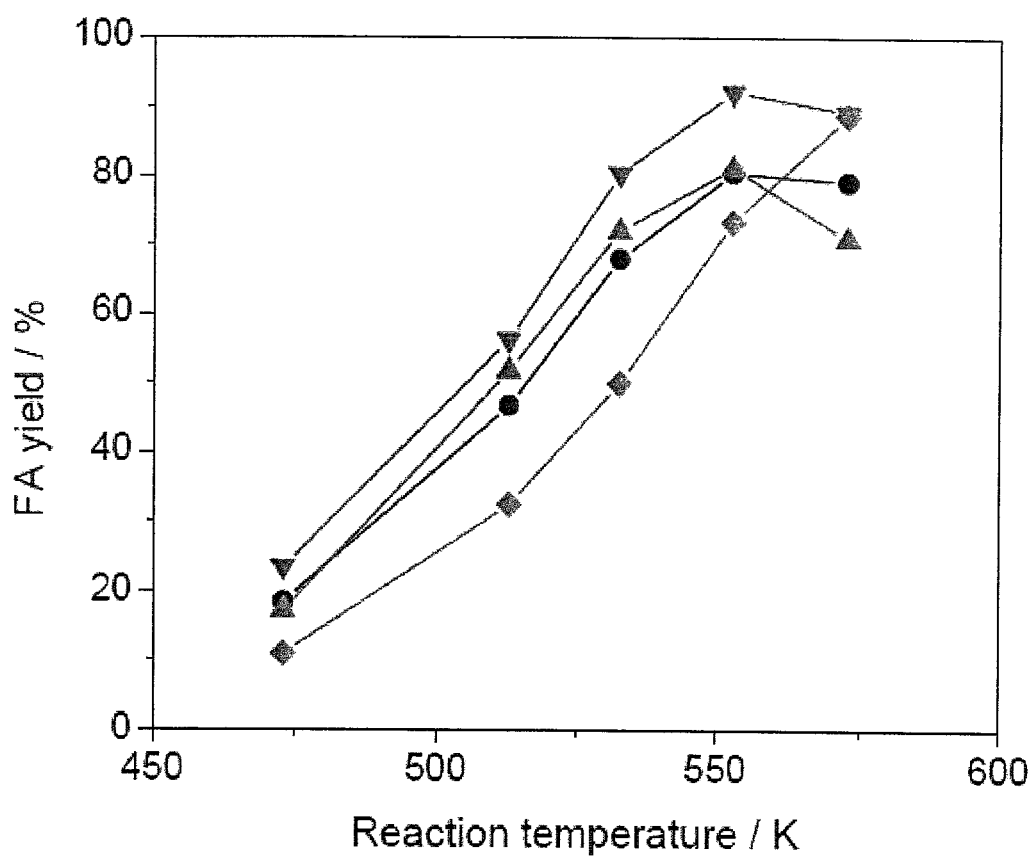

FIG. 3 compares the catalytic activity of an example of a catalyst in accordance with the present invention compared with conventional iron molybdate catalyst;

FIG. 4 shows the catalytic activity of the catalyst of FIGS. 2a-2d, along with the catalytic activity of several comparative catalysts; and FIG. 5 shows the effect of calcination temperature on the catalytic activity of the catalyst of FIGS. 2a-2d.

Figure 1:
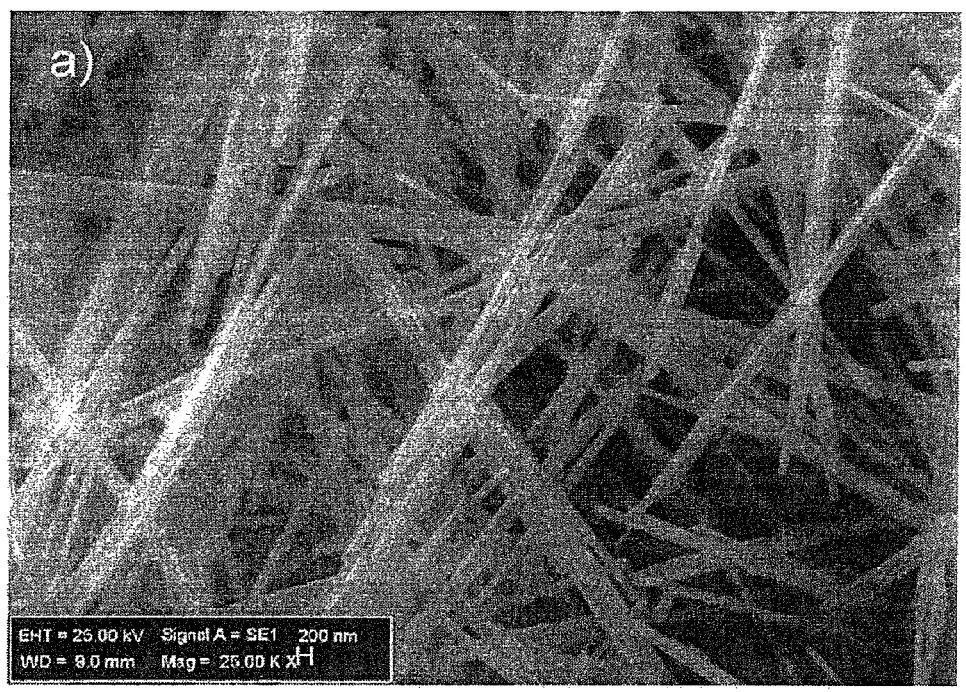
FIG. 1 is a scanning electron micrograph of precursor molybdate rods used to prepare an example of a catalyst in accordance with the present invention.
Figures 2A, 2B, 2C, 2D:
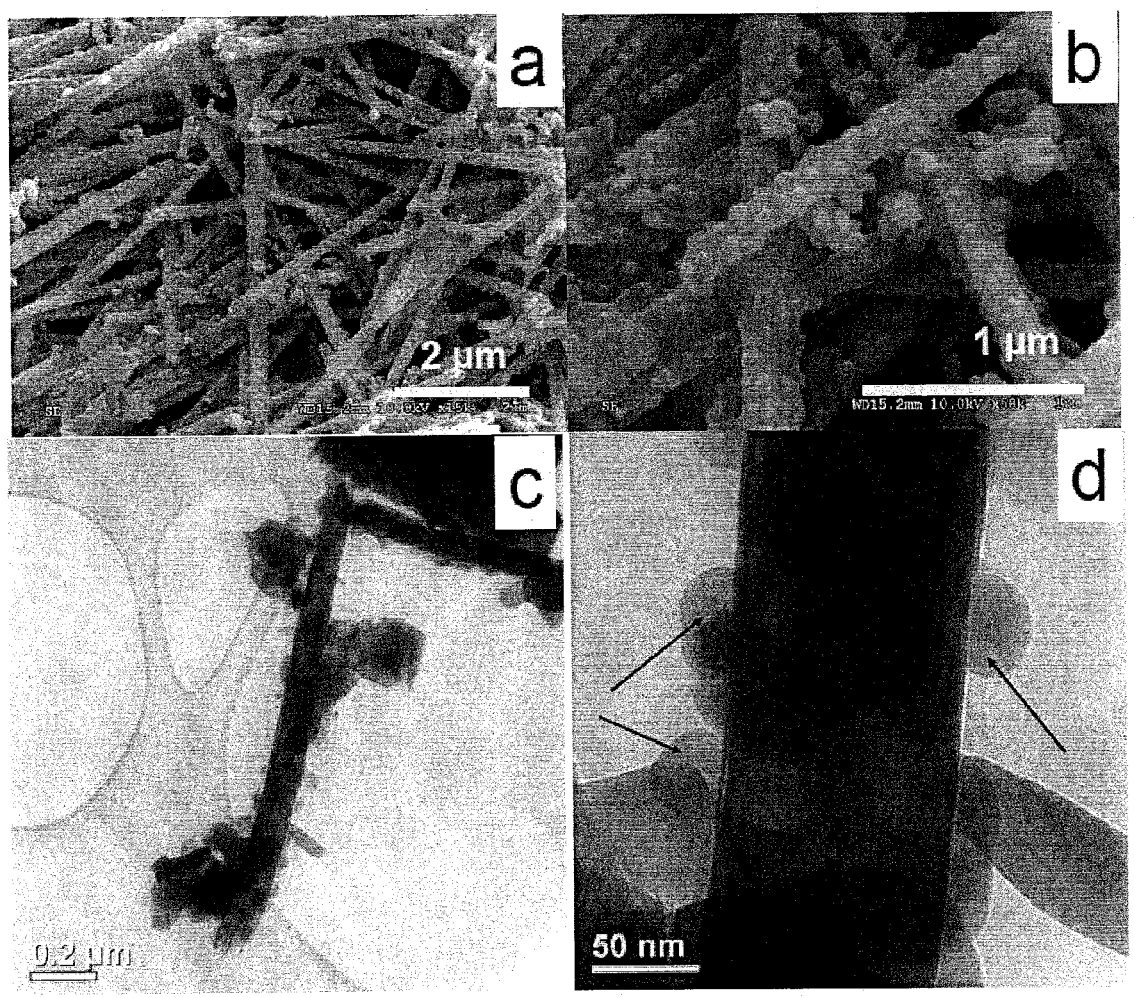
FIGS. 2a, 2b, 2c and 2d are scanning electron micrographs of a further example of a catalyst in accordance with the present invention.

The synthesis of an example of a catalyst in accordance with the present invention will now be described. Rods of molybdenum oxide were made as follows. 8 ml of 30% hydrogen peroxide solution (Sigma Aldrich, UK) was added to 1 g of commercially-available off-the-shelf molybdenum oxide ($MoO_3$, Sigma Aldrich, UK) in a glass beaker, and the mixture was stirred for 4-8 hours at 35° C. until all the $MoO_3$ had dissolved. 8 ml of water or 8 ml 2M $HNO_3$ was then added and the resulting mixture was autoclaved in a Teflon-lined autoclave at 170° C. for about 45 hours. The resulting solid (containing the rods of molybdenum oxide) was collected, washed thoroughly with deionised water and dried in a vacuum oven at 50-80° C. for 6-16 hours. FIG. 1 is a scanning electron micrograph of the rods of molybdenum oxide made as described. The molybdenum oxide rods had a mean length of about 5 to 10 microns and a mean dimension normal to the length of about 0.1-0.5 microns.

An iron nitrate solution ($Fe(NO_3)_3 \cdot 9H_2O$, Sigma Aldrich, UK) was added dropwise to (or sprayed onto) the rods of molybdenum oxide with stirring over a period of 5-10 minutes to form a slurry and the slurry was stirred. The mass of the water was approximately the same as the mass of the rods of molybdenum oxide. The preferred ratio of Mo:Fe was 1.5:1 to 6:1.

For example, 0.2-0.3 g of water was used to dissolve the appropriate amount of $Fe(NO_3)_3 \cdot 9H_2O$, and the solution added dropwise with constant stirring to 0.3 g of molybdenum oxide rods.

The resulting material was then dried in a vacuum oven at 50-90° C. for 2-16 hours and calcined in static air at a predetermined temperature (typically from 450° C. to 500° C.) for several hours (typically 2 hours) with a ramping rate of 2-5° C. $min^{-1}$. Examples of the catalyst in accordance with the present invention were manufactured, as indicated below, using the general method described above. The ratio of Mo:Fe was altered to investigate the effect of the ratio on structure and catalytic activity.

| Catalyst | Ratio of Mo:Fe |
| --- | --- |
| Catalyst 1 | 12:1 |
| Catalyst 2 | 6:1 |
| Catalyst 3 | 3.6:1 |
| Catalyst 4 | 2.2:1 |
| Comparative Catalyst 1 | $MoO_3$ rods |
| Comparative Catalyst 2 | Commercial iron molybdate catalyst |
| Comparative Catalyst 3 | 1.6:1, deposited onto $MoO_3$ rods (rod structure not maintained) |

Catalysts 1, 2, 3 and 4 were calcined at 500° C.

The structure of the catalysts was investigated using scanning electron microscopy and x-ray diffraction. Catalysts 1, 2, 3 and 4 showed the presence of islands of iron molybdate projecting from a rod of $MoO_3$. FIGS. 2a-2d show the structure of catalyst 4 as determined using scanning electron microscopy. The islands are particularly clearly seen in FIGS. 2b and 2d. The islands are in the form of projections or bulges. The islands are typically discrete i.e. separate from one another. Powder x-ray diffraction analysis indicated that catalysts 1, 2, 3 and 4 comprised iron molybdate and $MoO_3$, but no iron oxide.

Comparative Catalyst 3 was made using the same technique as that used to make catalysts 1, 2, 3 and 4, but using a higher iron content (the ratio of Mo:Fe being 1.6:1). Comparative Catalyst 3 showed an agglomerated structure, with no rod structure being retained.

FIG. 3 shows the catalytic activity of iron molybdate rods in accordance with the present invention in comparison to a commercially-available iron molybdate for the catalysis of the selective oxidation of methanol to methanal. The catalytic activity of the iron molybdate rods of the present invention was tested as follows.

Catalyst activity was determined in a fixed bed laboratory microreactor operated at atmospheric pressure as will be well known to those skilled in the art. 0.3 g of catalyst was placed in a quartz reactor tube and secured with quartz wool plugs. Methanol, oxygen and helium were passed over the catalyst with a total flow rate of 60 ml $min^{-1}$ with a $CH_3OH/O_2$/He ratio of 5/10/85. Product analysis was performed on-line using Gas Chromatography as is well known to those skilled in the art.

FIG. 3 shows the selectivity of the catalyst of the present invention and the commercially-available catalyst as a function of % conversion of methanol at various temperatures (■—commercially-available catalyst, ▲—example catalyst of the present invention). The number shown adjacent to each datum point is the temperature at which the catalysis was undertaken in ° C. As can be seen from FIG. 3, the example catalyst in accordance with the present invention compares favourably with the commercially-available catalyst.

Furthermore, it is expected that the example catalyst may be further optimised.

The catalytic activities of Catalysts 1, 2, 3 and 4 were compared to those of Comparative Catalysts 1, 2 and 3, substantially as described above. FIG. 4 shows the yield of formaldehyde as a function of reaction temperature (in kelvin) for each catalyst (-●—Catalyst 1; -▲—Catalyst 2; -STAR SHAPE—Catalyst 3; -FILLED DIAMOND SHAPE—Catalyst 4; -■—Comparative Catalyst 1; -○—Comparative Catalyst 2; -HEXAGON SHAPE—Comparative Catalyst 3)

The data indicate that each of Catalysts 1, 2, 3 and 4 perform better than the $MoO_3$ themselves. Furthermore, Catalysts 3 and 4 perform comparably to the commercially-available catalyst.

The effect of calcination temperature on the catalytic activity of the catalysts of the present invention was investigated using a catalyst in which the Mo:Fe ratio was 2.2:1.

| Catalyst | Calcination temperature (K) |
| --- | --- |
| Catalyst 4 | 773 |
| Catalyst 5 | 673 |
| Catalyst 6 | 723 |
| Catalyst 7 | 823 |

The catalytic activities of Catalysts 4, 5, 6 and 7 were investigated substantially as described above in relation to the catalysis of the formation of formaldehyde (methanal). FIG. 5 shows the yield of formaldehyde as a function of reaction temperature (in kelvin) for each catalyst (-INVERTED TRIANGLE SHAPE—Catalyst 4; -●—Catalyst 5; -▲—Catalyst 6; -FILLED DIAMOND SHAPE—Catalyst 7).

FIG. 5 shows that the activity of the catalyst of the present invention is sensitive to the calcination temperature.

It was determined, however, that calcination time did not strongly influence the catalytic activity of the catalyst of the present invention.

The example catalyst described above comprises iron molybdate. Those skilled in the art will realise that other metal molybdates may be used, such as manganese or cobalt molybdate. Furthermore, those skilled in the art will realise that the rods may comprise a metal molybdate (such as iron molybdate) and a further catalytic metal (for example, cobalt), possibly in the form of another metal molybdate (such as cobalt molybdate).

Where, in the foregoing description, integers or elements are mentioned which have known, obvious or foreseeable equivalents, then such equivalents are herein incorporated as if individually set forth. Reference should be made to the claims for determining the true scope of the present invention, which should be construed so as to encompass any such equivalents. It will also be appreciated by the reader that integers or features of the invention that are described as preferable, advantageous, convenient or the like are optional and do not limit the scope of the independent claims.

The invention claimed is:

1. A catalyst comprising rods having a mean length of 100 microns or less, the rods comprising molybdenum or tungsten oxide, from which project islands of metal molybdate or tungstate.

2. The catalyst according to claim 1 wherein the islands have a mean greatest dimension of from 10 to 100 nm and the mean density of said islands is from 20 to 100 islands per rod.

3. The catalyst according to claim 1 wherein said metal is selected from the group consisting of iron, manganese, bismuth, copper, nickel, chromium, vanadium, aluminium, silver, titanium and cobalt.

4. The catalyst according to claim 1 wherein the rods have a mean greatest dimension in a direction normal to the length of the rod of at least 0.1 microns.

5. The catalyst according to claim 1 wherein the ratio of the mean length of the rods to the mean greatest dimension in a direction normal to the length of the rod is from 3:1 to 100:1.

6. The catalyst according to claim 1 comprising a further metal catalyst, wherein the further metal catalyst is provided as a metal molybdate or metal oxide.

7. The catalyst according to claim 1 wherein the catalyst has a mean surface area of at least 5 $m^2g^-$.

8. The catalyst according to claim 7 having a mean surface area of at least 10 $m^2g^{-1}$ and wherein the metal molybdate or tungstate is iron molybdate or tungstate, and wherein the molar ratio of iron to molybdenum in the rods is from 0.01:1 to 0.3:1.

9. The catalyst according to claim 1 wherein the concentration of said metal is greater at the surface of the rods than in the centre of the rods.

10. The catalyst according to claim 1 comprising a central region and an outer region, the outer region having an innermost part and an outermost part wherein volume of the outer region is less than about 300% of the volume of the central region.

11. The catalyst according to claim 1 comprising a central region and an outer region, the outer region having an innermost part and an outermost part wherein concentration of said metal is higher in the outermost part of the outer region than in the innermost part of the outer region.

12. The method of making a catalyst according to claim 1, the method comprising:
   (i) Providing rods comprising molybdenum or tungsten oxide;
   (ii) Depositing metal on the rods comprising molybdenum or tungsten oxide; and
   (iii) Heating the product of step (ii) to produce rods comprising metal molybdate or tungstate.

13. The method according to claim 12 wherein the rods provided in step (i) comprise molybdenum (VI) oxide.

14. The method according to claim 12 wherein said metal is selected from the group consisting of iron, manganese, nickel, copper, bismuth, chromium, vanadium, aluminium, silver, titanium and cobalt.

15. The method according to claim 12 wherein the rods provided in step (i) are made by admixing particulate molybdenum (VI) oxide with hydrogen peroxide.

16. The method according to claim 12 wherein step (iii) comprises heating at a temperature of from 425° C. to 530° C.

17. A method for catalyzing a selective oxidation reaction. the method comprising:
   (a) providing in admixture an alcohol and a catalyst according to claim 1; and
   (b) allowing the reaction to proceed until the alcohol is oxidized. to an aldehyde.

18. A method for catalyzing a hydrodesuifurization reaction, the method comprising:
   (a) providing in admixture a sulfur-containing species, hydrogen or a source of hydrogen, and a catalyst according to claim 1; and
   (b) allowing the reaction to proceed until the sulfur is removed from the sulfur-containing species.

19. A method for catalyzing a hydrodenitrogenation reaction, the method comprising:
   (a) providing in admixture a nitrogen-containing species, hydrogen or a source of hydrogen and a catalyst according to claim 1; and
   (b) allowing the reaction to proceed until the nitrogen is removed from the nitrogen-containing species.

* * * * *